United States Patent

Roussouly et al.

Patent Number: 5,810,816
Date of Patent: Sep. 22, 1998

[54] DEVICE FOR STABILIZING ORTHOPEDIC ANCHORS

[76] Inventors: Pierre Roussouly, 34 rue du Ferroux, 69450 Saint Cyr Au Mont D'or; Gilbert Taglang, 9 rue Paul Verlaine, 67370 Griesheim sur Souffel; Arsëne Grosse, 5 rue des Fougères, 67400 Illkirch Graffenstaden; Daniel Chopin, 876 avenue Adolphe Leroy, 62155 Merlimont, all of France

[21] Appl. No.: 727,591
[22] PCT Filed: Apr. 19, 1995
[86] PCT No.: PCT/FR95/00507
  § 371 Date: Oct. 9, 1996
  § 102(e) Date: Oct. 9, 1996
[87] PCT Pub. No.: WO95/28889
  PCT Pub. Date: Nov. 2, 1995

[30] Foreign Application Priority Data

Apr. 20, 1994 [FR] France .................................. 94 05039

[51] Int. Cl.⁶ .................................................. A61B 17/58
[52] U.S. Cl. ................................ 606/61; 606/60; 606/72; 606/73; 606/75
[58] Field of Search ................................ 606/60, 61, 72, 606/73, 75

[56] References Cited

U.S. PATENT DOCUMENTS

| | | |
|---|---|---|
| 4,289,123 | 9/1981 | Dunn . |
| 4,793,335 | 12/1988 | Frey et al. ................................ 606/73 |
| 4,960,420 | 10/1990 | Goble et al. ............................... 606/75 |
| 4,988,351 | 1/1991 | Paulos et al. ............................. 606/72 |
| 5,269,784 | 12/1993 | Mast . |
| 5,314,427 | 5/1994 | Goble et al. ............................... 606/75 |
| 5,415,659 | 5/1995 | Lee et al. .................................. 606/61 |

FOREIGN PATENT DOCUMENTS

| | | |
|---|---|---|
| 2275679 | 1/1976 | France . |
| 2642642 | 8/1990 | France . |
| 2173104 | 10/1986 | United Kingdom . |
| 93/20771 | 10/1993 | WIPO . |
| 94/00062 | 1/1994 | WIPO . |

Primary Examiner—Michael Buiz
Assistant Examiner—Daphna Shai
Attorney, Agent, or Firm—William H. Eilberg

[57] ABSTRACT

The stabilizing device can be adapted to an anchor such as a hook (1) of the usual shape, with a hook body (4) and an incurved lug (7). The device including a stabilizing staple fastener (3) having a body (21) and staple legs (22–25). Said fastener body (21) is adapted so that the securing member secure the hook (1) to an attachment rod (52) also attach the fastener (3) to the hook (1), by forcing back the legs (22–25) in the direction of the incurved lug (7) so as to pierce a portion of the vertebra located in the hollow of the hook (1). The hook (1) is thereby effectively stabilized on the vertebra.

12 Claims, 7 Drawing Sheets

DEVICE FOR STABILIZING ORTHOPEDIC ANCHORS

TECHNICAL FIELD OF THE INVENTION

The present invention concerns anchors such as pedicle screws and hooks used for instrumentation of the spine, which are placed on the vertebrae to constitute anchor members linked together by one or more attachment rods.

The orthopedic hooks usually employed for instrumentation of the spine are shaped to hook onto a part of a vertebra. A hook of this kind comprises a hook body having an interior bearing face and an exterior fixing face provided with means for fixing it to an anchor point attachment rod, and a curved lug forming with the interior face of the body a U-shape profile to surround said part of a vertebra. The curved lug comprises a traction branch generally opposite the interior face of the body to which it is joined by a linking branch.

These orthopedic hooks used for instrumentation of the spine are placed on the vertebrae in three different ways.

In a first mode of use they are oriented upwards: they are slipped between two processes and the notched end of their lug bears on the pedicle of the vertebra with the hollow of their U-shape profile under the shoulder of the lower process and the lug on the inside.

In a second mode of use they are oriented upwards: they are slipped under the lamina of the vertebra and the hollow of their U-shape profile bears on the lower edge of the lamina of the vertebra.

In a third mode of use they are oriented downwards and the hollow of their U-shape profile bears on the upper edge of the lamina of the vertebra.

The problem is that, regardless of their position, the hooks have no or very little primary stability, i.e. they constitute a stable anchor member only on condition that they are combined with a second anchor member such as a another hook facing the opposite way or a fixing screw. Even in the presence of another anchor member facing the opposite way, a hook of this kind can slide medially on the lamina and escape from bearing engagement with the pedicle. It can turn inwards and enter the medullary canal of the vertebra, putting the spinal cord at risk.

In some cases anchorage is provided by a bone screw that is screwed into the pedicle of the vertebra. A pedicle screw of this kind has a screwthreaded external part with a close-pitched screwthread adapted to receive a nut, an anchor body or intermediate part of larger diameter and a coaxial screwthreaded internal part with a close-pitched screwthread adapted to screw into the pedicle and into the body of the vertebra. The screw is linked to a connecting rod by a clamp tightened by the nut screwed onto the screwthreaded external part. Alternatively, the screw is linked to a connecting plate or strip a portion of which has the screwthreaded external part of the screw passed through it and is clamped by the nut screwed onto said screwthreaded external part.

During the implementation step, the screwthreaded internal part is screwed into the bone, after which the connecting rod or plate is fitted to the screwthreaded external part and the nut is screwed on to reduce the deformation of the vertebrae and to fasten together the connecting rod or plate and the screw. Tightening the nut applies a torque to the pedicle screw which sometimes causes excessive tightening of the screw in the bone.

During reduction and during subsequent use the repeated movements of and stresses on the spine sometimes cause a small degree of unscrewing of the screwthreaded internal part, or axial withdrawal of the screw, or unseating due to repeated lateral stresses and oscillation that cause the screw to oscillate when only the intermediate part of its screwthreaded internal part is engaged in the cortical bone of the pedicle; this makes the anchorage fragile.

Documents GB-A-2 173 104 and FR-A-2 275 679 describe orthopedic anchor members in which a washer with short teeth is inserted between the anchor body and the bone of the vertebra, the teeth engaging in the bone. A washer of this kind does not prevent relative rotation and therefore does not achieve primary stabilization of the anchor.

Document U.S. Pat. No. 5,269,784 describes an anchor comprising a spreader nut. A spreader nut of this kind is not able to present rotation for the purpose of primary stabilization of the anchor.

SUMMARY OF THE INVENTION

The problem to which the present invention is addressed is that of achieving primary stabilization of the orthopedic anchorage to the vertebra, to improve the anchorage in the bone from the preliminary step of fitting instrumentation to the spine, during the step of reducing the deformation of the spine and throughout the subsequent period of supporting the spine. The aim is to achieve reliable and permanent stability of the anchorage, whether in the form of pedicle screws or hooks, to avoid short-term or medium-term losses of reduction. For this it is necessary to prevent all rotation and all oscillation of the anchor screw or all rotation and all translation of the anchor hook.

Stabilizing the hook on a vertebra is a delicate procedure. To stabilize the hook by means of a bone screw that is screwed into the vertebra, a solid part of the vertebra must be found to receive the screw: this is rarely possible; in particular, the bone of the lamina of the vertebra, which is naturally thin and fragile, is not adapted to receive a bone screw. An alternative solution is to provide two hooks facing in opposite direction and linked by a clamping device for moving them towards each other in the direction parallel to their interior bearing face. A solution of this kind is difficult to use because a proper bearing engagement must be obtained for both hooks simultaneously, and the lateral stabilization is insufficient.

The invention is aimed at achieving improved stabilization, preventing primary rotation of the hook under the zygapophysis and the pedicle of the vertebra, in the case of a pedicle hook. The invention is also directed to preventing primary rotation and primary translation of the hook on the lamina of the vertebra. This stabilization is achieved during and after the reduction of the deformation of the spine.

The invention is also directed to achieving primary stabilization of a pedicle screw, avoiding lateral oscillation of the screw, preventing it unscrewing from the bone and its excessive screwing into the bone, and preventing its withdrawal from the bone.

To achieve these and other objects, the device for stabilizing orthopedic anchors according to the invention is fitted to an anchor in the form of a hook or a screw. The anchor comprises:

an anchor body having an interior bearing face to bear against the vertebra and an opposite exterior fixing face, anchor means fastened to the anchor body and shaped to be fixed to the vertebra, a fixing part fastened to the anchor body and provided with means for fixing it to an anchor point attachment rod or plate.

The stabilizing device comprises a stabilizing staple fastener including:

a staple body adapted to engage on the exterior fixing face of the anchor body and provided with means for fastening it to the anchor body, opposing relative rotation between the staple body and the anchor body and selectively enabling movement towards each other of the staple body and the anchor body to a stabilization position bearing against the exterior fixing face and movement away from each other of the staple body and the anchor body to a released position, at least one staple leg fastened to the staple body, oriented and shaped to penetrate the vertebra beyond the interior bearing face of the anchor body when the stabilizing staple fastener is in a stabilizing position on the anchor body, itself in the anchor position on the vertebra.

In a first embodiment, the staple body is articulated to the anchor body about a transverse axis.

In a second embodiment, the stabilizing staple fastener is a removable member separate from the anchor, adapted to engage on the exterior fixing face of the anchor body.

In all cases, an anchor fixing part may advantageously be provided preventing relative axial rotation between the anchor body and the anchor point attachment rod. To this end, in an advantageous embodiment:

the anchor fixing part is a screwthreaded rod projecting from the exterior fixing face of the anchor body and adapted to receive a clamping stirrup and a nut, first anti-slip raised patterns are provided on the exterior fixing face of the anchor body, corresponding intermediate anti-slip raised patterns are provided on the two opposed faces of the staple body, and second anti-slip raised patterns are provided on a face of the clamping stirrup.

BRIEF DESCRIPTION OF THE DRAWINGS

Other objects, features and advantages of the present invention will emerge from the following description of specific embodiments given with reference to the appended drawings in which.

DESCRIPTION OF THE PREFERRED EMBODIMENTS

Figure 1:
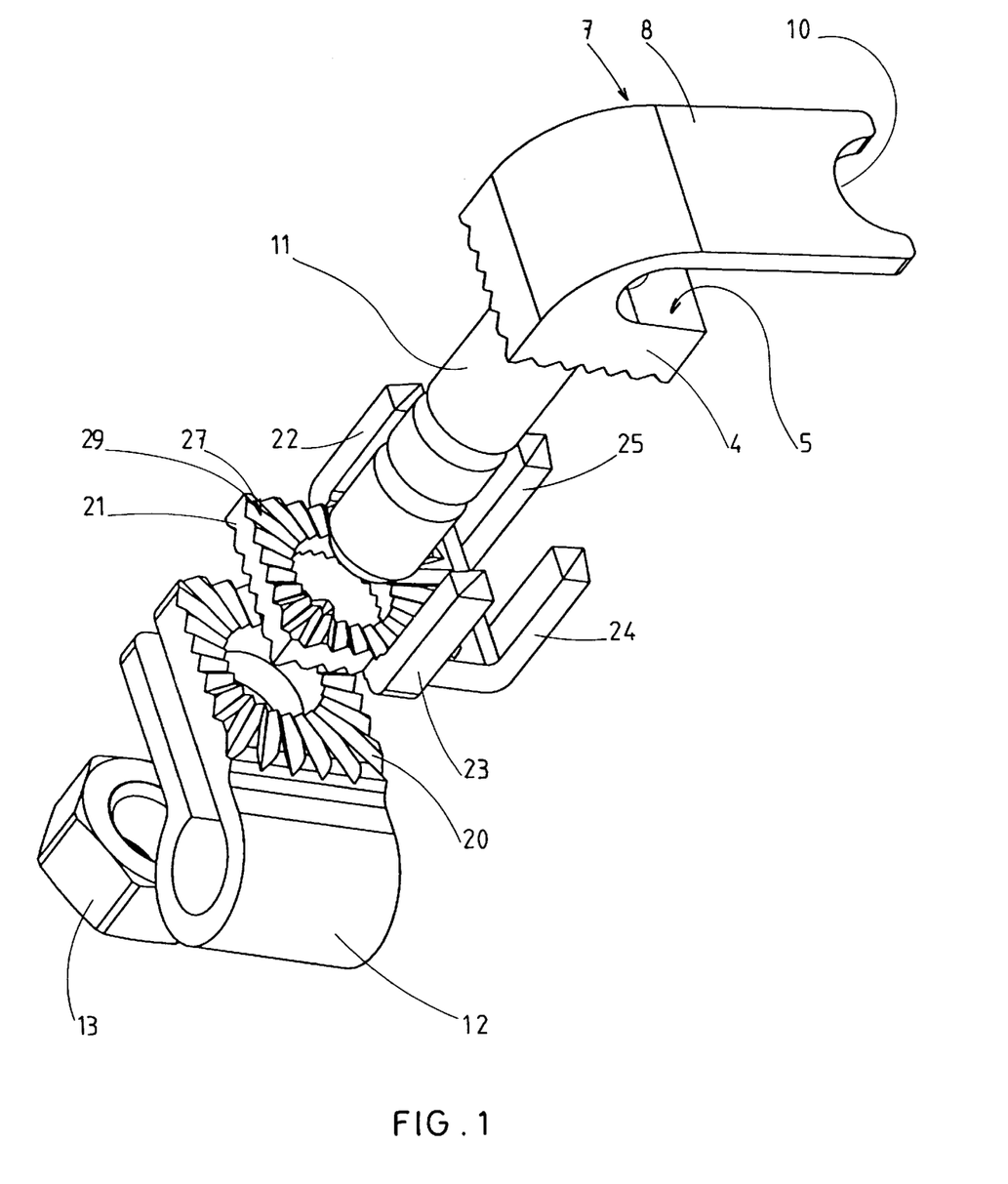
FIG. 1 is a first exploded perspective view of an anchor unit including an orthopedic hook and a first embodiment of stabilizing device of the invention.
Figure 2:
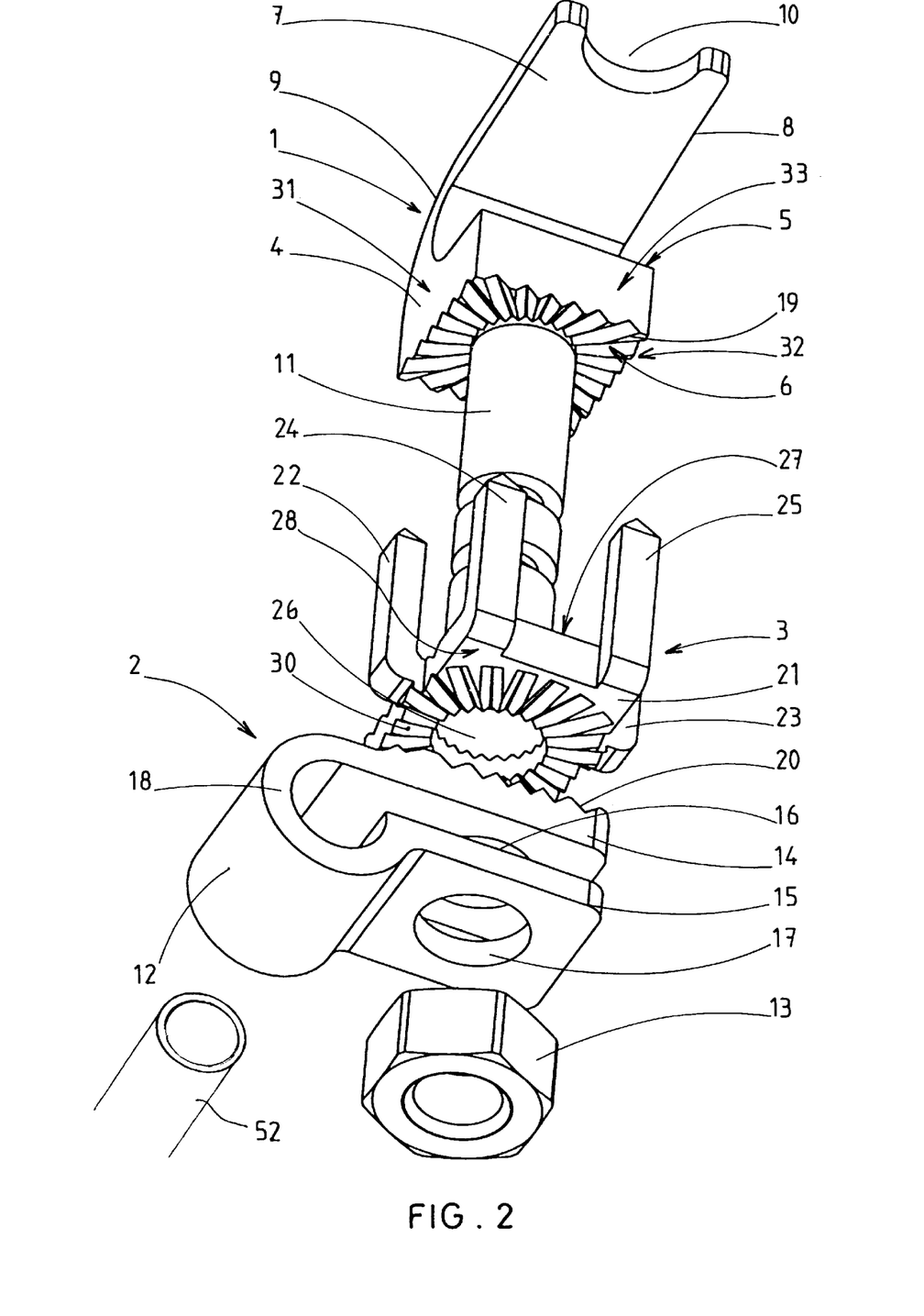
FIG. 2 is a second exploded perspective view of the device from FIG. 1.
Figure 3:
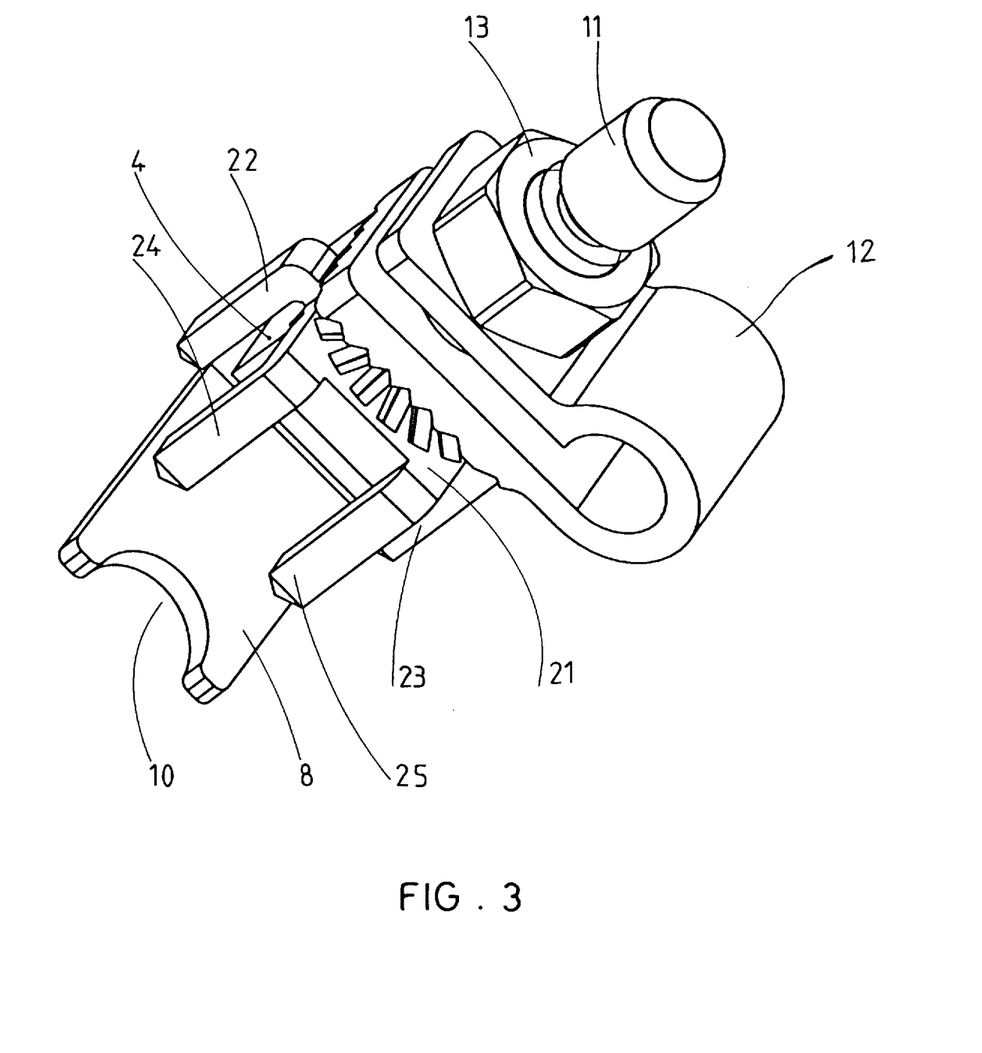
FIG. 3 is a perspective view of the device from FIG. 1 assembled in the anchorage position.

In the embodiment shown in FIGS. 1 to 3 an anchor unit with a hook stabilizing device of the invention comprises an orthopedic hook 1, means 2 for fixing the hook to an anchor point attachment rod 52 and a stabilizing device 3 for stabilizing the hook 1 on a vertebra.

The hook 1 comprises a hook body 4 having an interior bearing face 5 and an exterior fixing face 6 provided with means 2 for fixing it to the attachment rod 52. The hook 1 further comprises a curved lug 7 forming with the interior face 5 of the hook body 4 a U-shape profile adapted to surround a part of the vertebra to which the hook 1 is to be anchored. The curved lug 7 has a traction branch 8 generally opposite and parallel to the interior bearing face 5 of the hook body 4, to which it is joined by a linking branch 9. The free end of the traction branch 8 advantageously comprises a notch 10 adapted to favor location of the hook under the zygapophysis and the pedicle of a vertebra.

In the embodiment shown in the figures, the fixing means 2 comprise a screwthreaded fixing rod 11 projecting from the exterior fixing frame 6 of the hook body 4 and adapted to receive a clamping stirrup 12 and a nut 13. The clamping stirrup 12 has two branches 14 and 15 provided with respective holes 16 and 17 for the fixing rod 11 to pass through, the parallel branches 14 and 15 being joined to each other by a curved intermediate part 18 adapted to surround a part of the attachment rod 52. By tightening the nut 13 the branches 14 and 15 of the clamping stirrup 12 are moved closer together to clamp the stirrup 12 to the attachment rod 52 to fasten the hook 1 to said attachment rod 52.

To oppose rotation of the hook 1 relative to the attachment rod 52, first anti-slip raised patterns 19 are provided on the exterior fixing face 6 of the hook body 4 and second anti-slip raised patterns 20 are provided on the corresponding face of the branch 14 of the clamping stirrup 12.

This embodiment of the stabilizing device 3 shown in FIGS. 1 to 3 comprises a stabilizing staple fastener having a staple body 21 provided with means for fastening it to the hook body 4 and four staple legs 22, 23, 24 and 25 attached to the staple body 21 and extending perpendicularly to the staple body 21 in the same direction. The staple leg or legs 22–25 attached to the staple body 21 extend inside the U-shape profile towards the traction branch 8 substantially perpendicular to the interior bearing face 5 of the hook body 4 to penetrate into said part of the vertebra in the supporting position.

In the embodiment shown, in the position holding the staple fastener 3 onto the hook 1, the free end of the legs 22–25 is slightly set back from the traction branch 8 of the hook 1.

The means for fastening the staple body 21 to the hook body 4 utilize the fixing rod 11 that passes through a hole 26 in the staple body 21, the fixing rod 11 being then substantially parallel to the four legs 22–25 of the staple fastener. To use it, the staple body 21 is placed around the fixing rod 11 and on the exterior fixing face 6, with the legs 22–25 directed towards the hook 1. The means for fastening the staple body 21 to the hook body 4 thus enable relative displacement of the staple body 21 towards and away from the hook body 4, between a retracted position in which the legs 22–25 are away from the curved lug 7 of the hook and a stabilization position shown in FIG. 3 in which the legs 22–25 extend inside the U-shape profile of the hook 1 towards the traction branch 8, substantially perpendicularly to the interior bearing face 5 of the hook body 4, to penetrate into the part of the vertebra inserted into the hollow of the hook 1. In the stabilization position, the first face 27 of the staple body 21 bears on the exterior fixing face 6 of the hook body 4 and the staple body 21 is pushed towards the hook 1 by the clamping stirrup 12, the bearing face of which with anti-slip raised patterns 20 thereon coming to bear on the second face 28 of the staple body 21. To oppose relative rotation between the hook 1 and the clamping stirrup 12 attached to the attachment rod, third anti-slip raised pattern 29 are provided on the first face 27 of the staple body 21 with fourth anti-slip raised patterns 30 on the second face 28 of the staple body 21.

The legs 22–25 are so positioned that the stabilization device straddles the hook body 4. In the embodiment shown the legs 22 and 23 are two lateral legs disposed to project beyond lateral edges 31 and 32 of the hook body 4. The legs 24 and 25 are two front legs extending beyond the edge of the free end 33 of the hook body 4.

Figure 4:
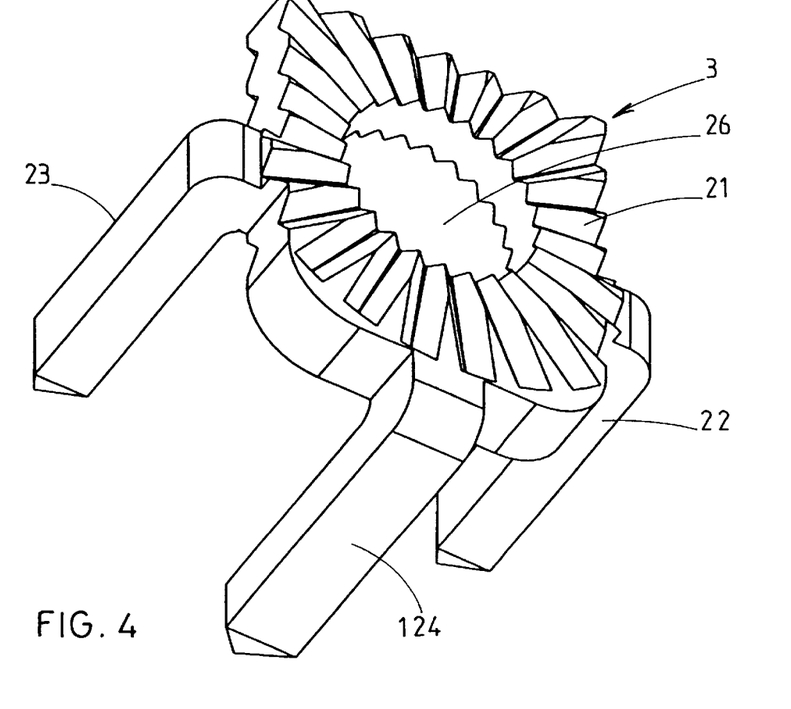
FIG. 4 is a perspective view showing a second embodiment of an orthopedic hook stabilizing device of the invention.

FIG. 4 shows a slightly different embodiment of the stabilization device 3 having a staple body 21 similar to the staple body from FIGS. 1 to 3 and two lateral staple legs 22 and 23 similar to the lateral legs of the embodiment of FIGS. 1 to 3. The difference is that the stabilization device 3 of FIG. 4 comprises only one front leg 124, disposed substantially centrally as shown in the figure.

In the embodiments of FIGS. 1 to 4, the stabilizing staple fastener constitutes a removable part separate from the hook 1, adapted to engage on the exterior fixing face 6 of the hook body 4.

Figure 5:
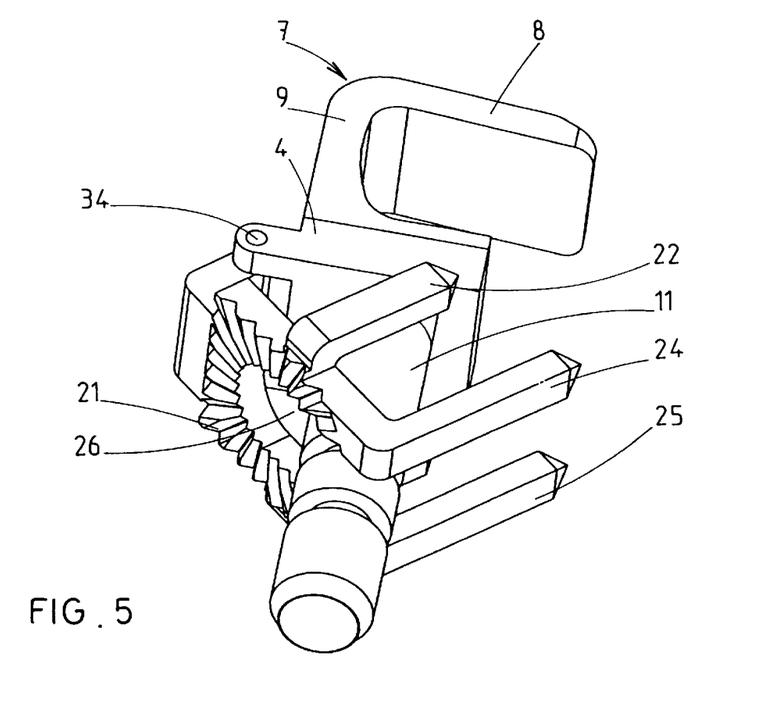
FIG. 5 is a perspective view showing an anchor unit and another embodiment of a stabilizing device of the invention.

FIG. 5 shows a different embodiment of the invention in which the staple body 21 is articulated to the hook body 4 about a transverse axis 34 near the part jointing the hook body 4 to the curved lug 7. The hole 26 in the staple body 21 through which the fixing rod 11 passes is open between the front legs 24 and 25 to enable the staple fastener to tilt as shown in the figure.

Otherwise, the anchor device of FIG. 5 comprises he same components as the anchor device of FIGS. 1 to 3 and these components are identified by the same reference numbers.

Figure 6:
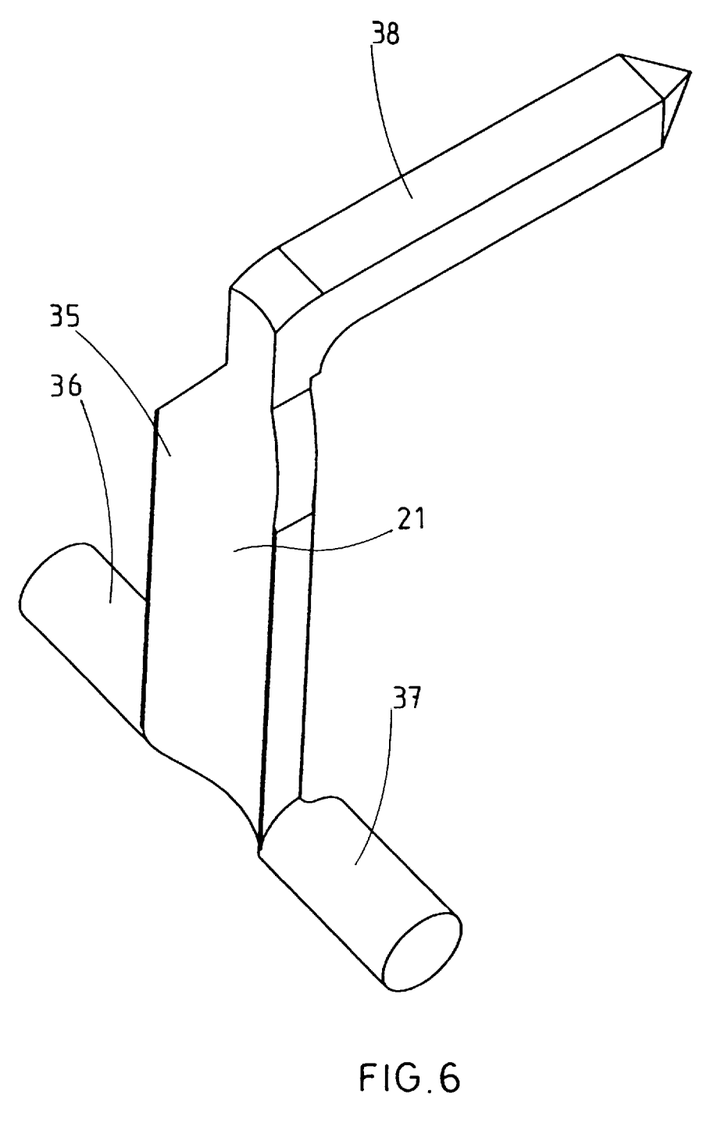
FIG. 6 is a perspective view of another embodiment of an orthopedic hook stabilizing device of the invention.
Figure 7:
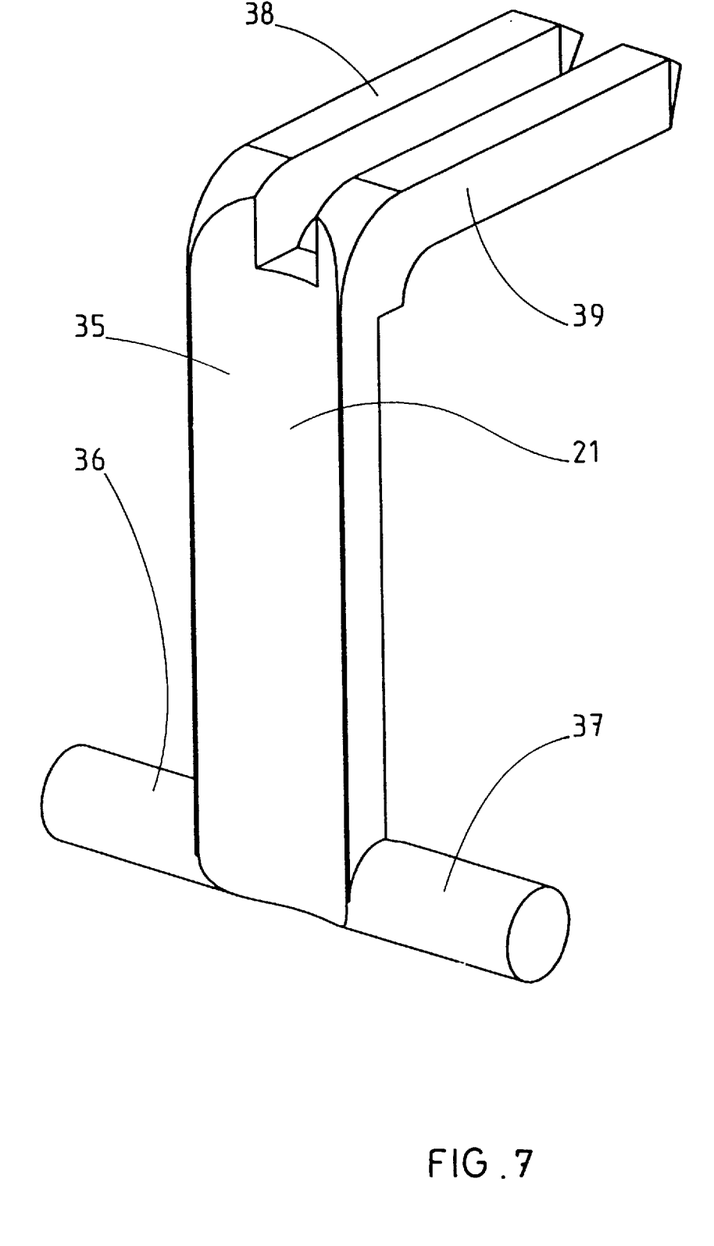
FIG. 7 is a perspective view of another embodiment of an orthopedic hook stabilizing device of the invention.

FIGS. 6 and 7 show two other embodiments of the stabilizing device 3 of the invention for stabilizing a hook 1 on the vertebrae. In FIG. 6, the staple body 21 is T-shape with a central branch 35 and two lateral branches 36 and 37 of circular cross-section. The staple body is joined to a single front leg 38. A staple fastener of this shape is designed to fit to hooks in which the means of fixing them to an attachment rod comprise a hook body having a diametral slot through which the attachment rod passes, with means for clamping the rod into the hook body. The shape of the staple body 21 enables it to be inserted into the diametral slot through which the attachment rod passes.

The FIG. 7 embodiment uses the same shape staple body 21 with a central branch 35 and two lateral branches 36 and 37. The difference is that there are two front legs 38 and 39 which are parallel to each other, as shown in the figure.

In all the embodiments described above, the staple body 21 is such that the means for fixing the hook 1 to an attachment rod also fasten the staple fastener 3 to the hook 1, by pushing the legs 22–25 towards the curved lug 7 to penetrate a part of a vertebra inserted into the hollow of the hook 1. This achieves efficient primary stabilization of the hook 1 on a vertebra.

Figure 8:
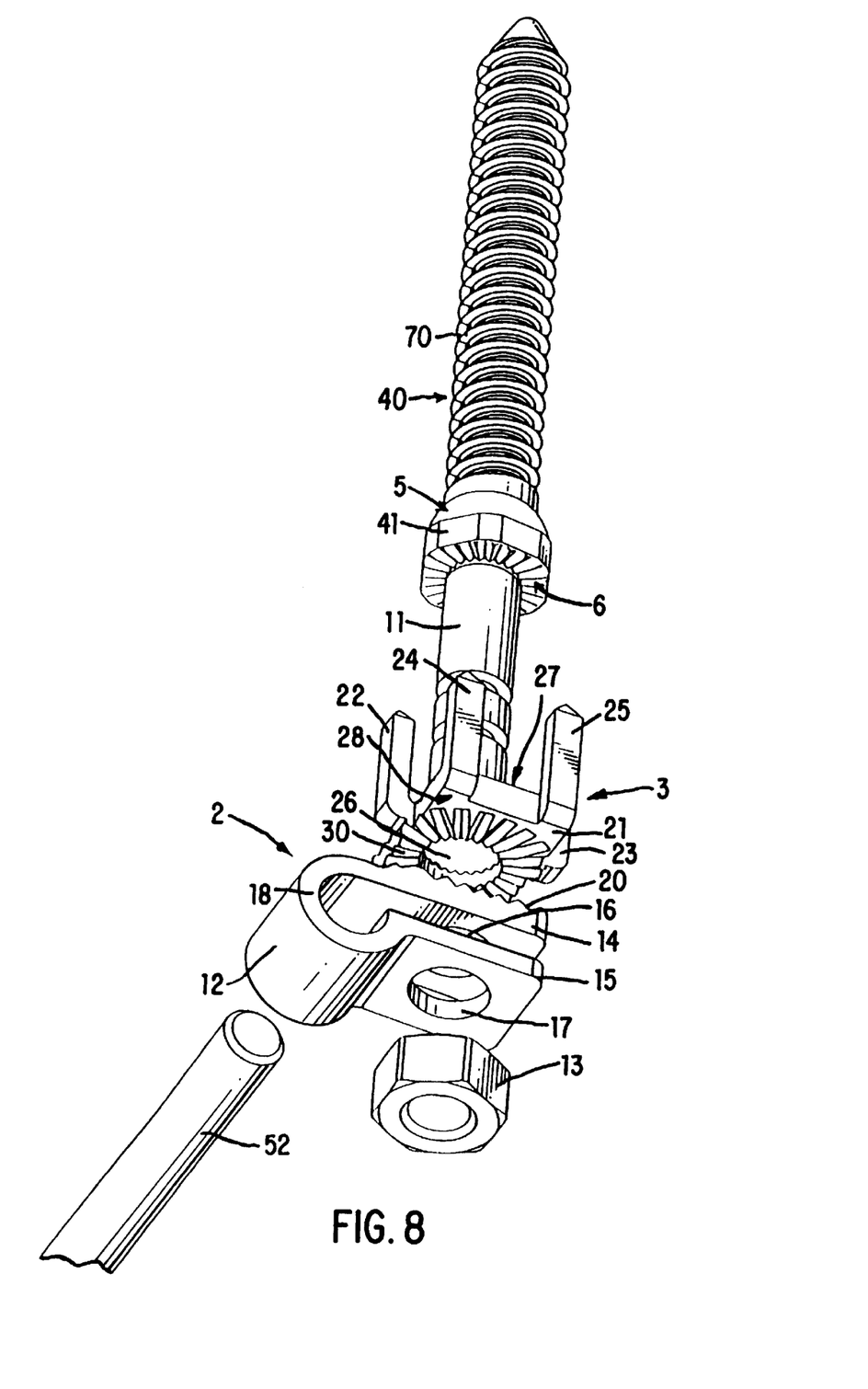
FIG. 8 is a perspective view showing a stabilizing staple fastener in an embodiment adapted to stabilize a pedicle screw.

In the embodiment shown in FIG. 8 the stabilization device of the invention is adapted to stabilize an anchorage provided by a pedicle screw 40. The pedicle screw 40 comprises an anchor body 41 with an interior bearing face 5 and an exterior fixing face 6 and a screwthreaded internal rod 70 adapted to screw into the bone of the vertebra, with fixing means including a coaxial screwthreaded external rod 11 adapted to have a nut 13 screwed onto it to clamp a clamping stirrup 12 onto an anchor point attachment rod 52.

To stabilize a pedicle screw anchorage of this kind, a stabilizing staple fastener 3 is used, for example with four legs 22–25 as shown in FIG. 8, of the same design as in the embodiment of FIGS. 1 to 3. The staple fastener leg or legs 22–25 attached to the staple body 21 extend axially around the anchor body 41 and beyond the interior bearing face 5 to penetrate the bone of the vertebra when the anchorage is in position on the vertebra with the staple fastener 3 bearing on the exterior fixing face 6.

The stabilizing staple fasteners shown in the figures enable an orthopedic anchor member to be provided for instrumentation of the spine comprising an orthopedic anchor 1 such as a hook or a pedicle screw and a stabilizing staple fastener 3.

In accordance with the invention, there is obtained in this way spinal therapy apparatus comprising at least one attachment rod or plate 52 linking anchor units adapted to be fixed to the vertebrae of the spine, and at least one of the anchor units comprising an orthopedic anchor 1 such as a hook or a pedicle screw and a stabilizing staple fastener 3.

The invention is not limited to the embodiments that have been explicitly described, but includes variants and generalizations thereof within the scope of the following claims.

We claim:

1. Device for stabilizing orthopedic anchors on a vertebra, for Instrumentation of the spine, the device comprising an anchor which includes;

an anchor body having an interior bearing face to bear against the vertebra and an opposite exterior fixing face, anchor means connected to the anchor body and shaped to be fixed to the vertebra, and a fixing part connected to the anchor body and provided with means for fixing it to an anchor point attachment rod or plate the stabilizing device comprising a stabilizing staple fastener including:

a staple body which engages the exterior fixing face of the anchor body and provided with means for fastening it to the anchor body, opposing relative rotation between the staple body and the anchor body and selectively enabling movement towards each other of the staple body and the anchor body to a stabilization position bearing against the exterior fixing face and movement away from each other of the staple body and the anchor body to a released position, and at least one staple leg fastened to the staple body, oriented and shaped to penetrate the vertebra beyond the interior bearing face of the anchor body when the stabilizing staple fastener is in a stabilizing position on the anchor body, itself in the anchor position on the vertebra.

2. The device of claim 1 wherein the staple body is articulated to the anchor body about a transverse axis.

3. The device of claim 1 wherein the stabilizing staple fastener is a removable member separate from the anchor, adapted to engage on the exterior fixing face of the anchor body.

4. The device of claim 1 wherein:

the anchor fixing part is a screwthreaded rod projecting from the exterior fixing face of the anchor body and adapted to receive a clamping stirrup and a nut, first anti-slip raised patterns are provided on the exterior fixing face of the anchor body, corresponding intermediate anti-slip raised patterns are provided on the two opposed faces of the staple body, and second anti-slip raised patterns are provided on a face of the clamping stirrup.

5. The device of claim 1 wherein:

the anchor is a hook having a hook body including an interior bearing face and an exterior fixing face provided with means for fixing it to an anchor point attachment rod and a curved lug forming with the interior face of the hook body a U-shape profile to surround a part of the vertebra with a traction branch generally opposite and parallel to the interior bearing face of the hook body to which it is joined by a linking branch, and the staple leg or legs fastened to the staple body extend inside the U-shape profile towards the traction branch substantially perpendicular to the interior bearing face of the hook body to penetrate said part of the vertebra in the supporting position.

6. The device of claim 5 wherein the stabilizing staple fastener comprises two lateral legs extending beyond the lateral edges of the hook body and at least one front leg extending beyond the edge of the free end of the hook body.

7. The device of claim 5 wherein the stabilizing staple fastener comprises two lateral legs projecting beyond the lateral edges of the hook body and two front legs projecting beyond the edge of the free end of the hook body.

8. The device of claim 5 wherein the legs have a length such that, in the position in which the staple fastener is secured to the hook, the free end of the legs is slightly set back from the traction branch of the hook.

9. The device of claim 1 wherein:

the anchor is a pedicle screw comprising an anchor body with an interior bearing face and an exterior fixing face with an internal screwthreaded rod adapted to be screwed into the bone of the vertebra and with means for fixing it to an anchor point attachment rod, the staple leg or legs fastened to the staple body extend axially around the anchor body and beyond the interior bearing face to penetrate into the bone of the vertebra when the anchor is in position on the vertebra with the staple fastener bearing on the exterior fixing face.

10. Orthopedic anchor unit for instrumentation of the spine comprising an orthopedic anchor and a stabilizing staple fastener as claimed in claim 1.

11. Spine therapy apparatus comprising at least one attachment rod or plate linking anchor units adapted to be fixed to the vertebrae of the spine, wherein at least one of the anchor units comprises an orthopedic anchor and a stabilizing staple fastener as claimed in claim 1.

12. Device for stabilizing orthopedic anchors on a vertebra, for instrumentation of the spine, the anchor comprising:

an anchor body having an interior bearing face to bear against the vertebra and an opposite exterior fixing face, anchor means fastened to the anchor body and shaped to be fixed to the vertebra, and a fixing part fastened to the anchor body and provided with means for fixing it to an anchor point attachment rod or plate, and the stabilizing device comprising a stabilizing staple fastener including:

a staple body adapted to engage on the exterior fixing face of the anchor body and provided with means for fastening it to the anchor body, opposing relative rotation between the staple body and the anchor body and selectively enabling movement towards each other of the staple body and the anchor body to a stabilization position bearing against the exterior fixing face and movement away from each other of the staple body and the anchor body to a released position, and at least one staple leg fastened to the staple body, oriented and shaped to penetrate the vertebra beyond the interior bearing face of the anchor body when the stabilizing staple fastener is in a stabilizing position on the anchor body, itself in the anchor position on the vertebra, wherein the staple body is articulated to the anchor body about a transverse axis.

* * * * *